(12) United States Patent
Völker et al.

(10) Patent No.: US 7,965,167 B2
(45) Date of Patent: Jun. 21, 2011

(54) INDUCTIVE CONDUCTIVITY SENSOR

(75) Inventors: Marco Völker, Karlsruhe (DE); Andreas Eberheim, Waldheim (DE); Torsten Pechstein, Radebeul (DE)

(73) Assignee: Endress + Hauser Conducta Gesellschaft für Messund Regeltechnik mbH + Co. KG, Gerlingen (DE)

( * ) Notice: Subject to any disclaimer, the term of this patent is extended or adjusted under 35 U.S.C. 154(b) by 0 days.

(21) Appl. No.: 12/010,915

(22) Filed: Jan. 31, 2008

(65) Prior Publication Data

US 2008/0218302 A1   Sep. 11, 2008

Related U.S. Application Data

(60) Provisional application No. 60/924,775, filed on May 31, 2007.

(30) Foreign Application Priority Data

May 29, 2006   (DE) .......................... 10 2006 025 194

(51) Int. Cl.
*H01F 27/28* (2006.01)
(52) U.S. Cl. ........................................ 336/229; 324/445
(58) Field of Classification Search .................. 336/229; 324/445, 654
See application file for complete search history.

(56) References Cited

U.S. PATENT DOCUMENTS

| | | | | |
|---|---|---|---|---|
| 3,292,077 A * | 12/1966 | Sloughter | ..................... | 324/445 |
| 3,603,873 A | 9/1971 | Cirulis | | |
| 3,806,798 A * | 4/1974 | Gross | ............................ | 324/445 |
| 3,867,688 A * | 2/1975 | Koski | ............................ | 324/445 |
| 4,220,920 A * | 9/1980 | Gross | ............................ | 324/442 |
| 5,430,613 A * | 7/1995 | Hastings et al. | ............... | 361/760 |
| 5,959,455 A * | 9/1999 | Brown | ........................... | 324/445 |
| 6,181,130 B1 * | 1/2001 | Hoshi et al. | .................... | 324/253 |
| 7,106,162 B2 * | 9/2006 | Saito | ............................. | 336/229 |
| 7,253,711 B2 * | 8/2007 | Pleskach et al. | .............. | 336/200 |
| 7,304,558 B1 * | 12/2007 | Pleskach et al. | .............. | 336/200 |
| 7,423,884 B2 * | 9/2008 | Enchi et al. | .................... | 361/761 |
| 7,479,864 B2 * | 1/2009 | Weller et al. | ................... | 336/200 |
| 7,513,031 B2 * | 4/2009 | Pleskach et al. | ............... | 29/606 |
| 7,616,088 B1 * | 11/2009 | Baker et al. | .................... | 336/229 |
| 2004/0178875 A1* | 9/2004 | Saito | ............................. | 336/200 |
| 2004/0179383 A1 | 9/2004 | Edo | | |
| 2005/0005424 A1* | 1/2005 | Nuytkens et al. | ............ | 29/602.1 |
| 2006/0227518 A1 | 10/2006 | Nishio | | |

FOREIGN PATENT DOCUMENTS

| | | |
|---|---|---|
| DE | 199 56 636 A1 | 10/2000 |
| DE | 103 34 830 A1 | 5/2005 |
| DE | 10 2005 014 929 A1 | 10/2006 |
| DE | 10 2006 025 194 A1 | 12/2007 |
| EP | 0 999 441 A1 | 5/2000 |
| WO | WO 2007/024322 A2 | 3/2007 |

* cited by examiner

*Primary Examiner* — Anh T Mai
*Assistant Examiner* — Joselito Baisa
(74) *Attorney, Agent, or Firm* — Bacon & Thomas, PLLC

(57) ABSTRACT

A conductivity sensor for measuring conductivity of a medium surrounding the conductivity sensor includes a first toroidal coil bounding a medium-receiving passageway and serving for inducing an electrical current in the medium, and a second toroidal coil also bounding the passageway and serving for registering a magnetic field produced by the electrical current. At least one of the toroidal coils has a plurality of first conductor segments, which extend in a plane of a multi-ply circuit board, a plurality of second conductor segments, which extend in a second plane of the circuit board, and a plurality of through-contacts, which connect the first conductor segments with the second conductor segments, wherein the first conductor segments, the second conductor segments and the through-contacts form, together, the windings of a toroidal coil.

29 Claims, 2 Drawing Sheets

INDUCTIVE CONDUCTIVITY SENSOR

This application is a Nonprovisional Application which claims the benefit of U.S. Provisional Application Ser. No. 60/924,775 filed on May 31, 2007.

TECHNICAL FIELD

The present invention relates to an inductive conductivity sensor.

BACKGROUND DISCUSSION

Inductive conductivity sensors for ascertaining electrical conductivity of a medium include, essentially, two toroidal coils, surrounded by the medium. The coils bound a passageway for the medium and are usually arranged coaxially, with a first of the coils, as exciter coil, inducing an electrical current in the medium. Such electrical current is then registered by the second coil. The principle, per se, is established in industrial process measurements technology and documented in a large number of examples of the patent literature, for example in U.S. Pat. No. 3,603,873 and German Offenlegungsschrift DE 198 51 146 A1.

SUMMARY OF THE INVENTION

An object of the invention is to provide an inductive conductivity sensor of improved sensitivity. Sensitivity of inductive conductivity sensors increases, on the one hand, with increasing cross sectional area of the passageway bounded by the toroidal coils, and decreases, on the other hand, with increasing length of the passageway, since the path length for the electrical eddy current induced in the medium by the coil increases with the axial length. The cross sectional area of the passageway can, however, not be arbitrarily increased for a given manner of coil construction, without increasing the total structural size of the conductivity sensor. As a result, it is desirable, for improving sensitivity, to reduce the axial length of the passageway. The object is achieved according to the invention by the conductivity sensor as defined in claim 1.

To this end, the invention provides an inductive conductivity sensor with a new type of coil construction, which makes possible an especially small axial length for the conductivity sensor. According to a further point of view of the invention, the new type of coil construction enables a simplified automated manufacture.

The inductive conductivity sensor of the invention for measuring conductivity of a medium includes:

A first toroidal coil bounding a passageway and serving for inducing electrical eddy current in a medium and a second toroidal coil also bounding the passageway and serving for registering a magnetic field produced by the eddy current, with at least one of the toroidal coils having a plurality of first conductor segments, which extend in a plane of a multi-ply circuit board, a plurality of second conductor segments, which extend in a second plane of the circuit board, and a plurality of through-contacts, which connect the first conductor segments with the second conductor segments, wherein the first conductor segments, the second conductor segments and the through-contacts form, together, the windings of the at least one toroidal coil. The term "circuit board" is intended to include structures forming examples of circuit boards, one such example being a circuit card.

The through-contacts extend, in a currently preferred embodiment of the invention, essentially perpendicularly to the plies of the circuit board.

The first and second conductor segments can, in each case, be embodied as conductive traces, or conductor paths, on an outer surface of the circuit board or in an intermediate ply in the circuit board.

The toroidal coil can be embodied as an air coil or as a ring-core coil, with the ring core being located, for example, in a corresponding cavity in the circuit board between the first and second planes.

The ring core can comprise, for example, a solid ring core, a wound tape, or band, ring core, or a plastic ring core containing magnetic particles. The ring core can, for example, during manufacture of the circuit board, be embedded, or laminated, into the cavity provided therefor, or, in the case of the plastic ring core, it can also be injected after manufacture of the circuit board, into cavities provided therefor in the circuit board.

In a currently preferred embodiment of the invention, both toroidal coils are built in the above-described manner.

The two coils can be arranged coaxially and axially shifted with respect to one another, or they can be arranged coaxially and coplanarly, with, in the second alternative, the coils having different radii. The coils are preferably shielded magnetically and capacitively from one another with usual shielding means.

At least the part of the sensor wettable by the medium can be covered, for example, with an insulating, protective layer, such as a coating, especially a plastic layer, such as a plastic coating, in order to protect the circuit board and the coils from direct contact with media.

Furthermore, electronic circuits can be provided on the circuit board for operation of the sensor.

BRIEF DESCRIPTION OF THE DRAWINGS

The invention will now be explained on the basis of examples of embodiments presented in the drawings, the figures of which show as follows.

DETAILED DISCUSSION

Figure 1:
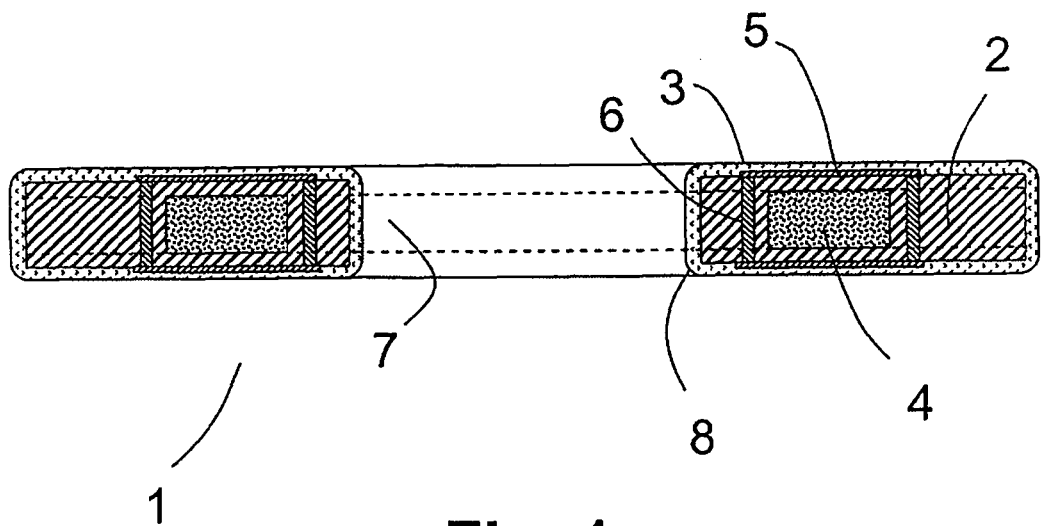
FIG. 1 a longitudinal section through a circuit board with a toroidal coil according to one embodiment of the invention.
Figure 2:
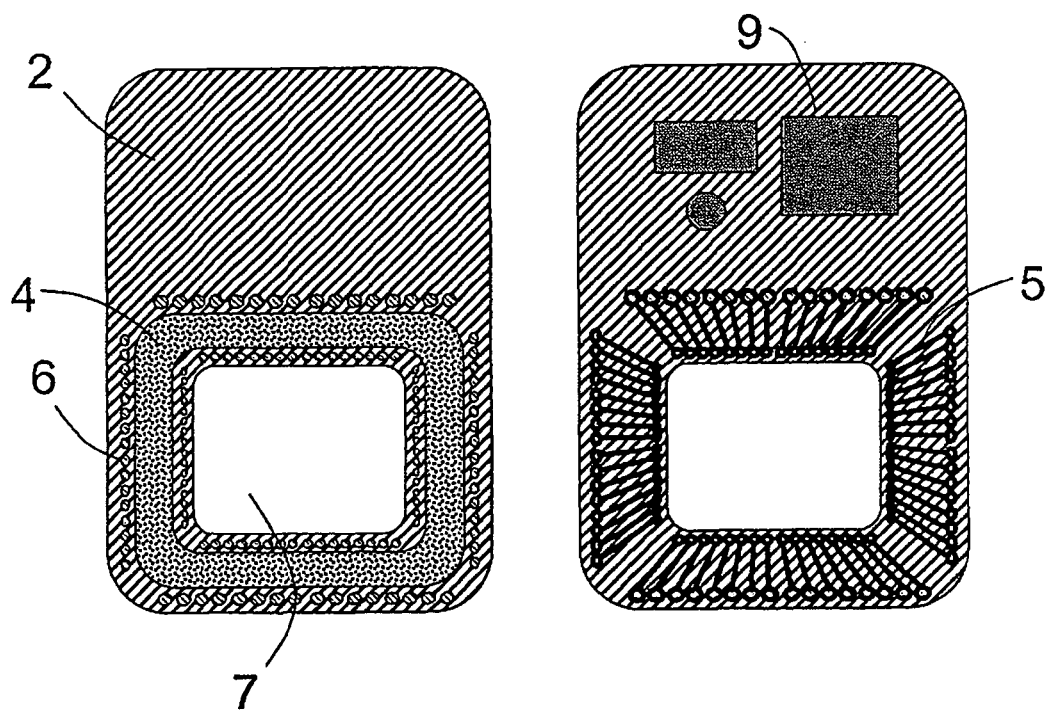
FIG. 2 a view of different planes of the circuit board of FIG. 1.

FIG. 1 shows a longitudinal section of a coil arrangement 1 for a conductivity sensor in a multi-ply circuit board 2. A view of different plies of this multi-ply circuit board 2 of the coil arrangement is shown in FIG. 2, wherein the left portion of the figure shows an intermediate ply and the right portion a cover ply. The coil arrangement will now be explained with reference to FIGS. 1 and 2.

Coil arrangement 1 includes a toroidal coil 3, which annularly bounds a passageway 7 in the circuit board 2. The toroidal coil 3 includes first conductor segments 5, which extend on the upper side of the cover ply, and second conductor segments, which extend on the underside of a base ply of the circuit board. Between the base ply and the cover ply, an intermediate ply is arranged, which itself can include one or more plies. The intermediate ply includes a cavity in which a tape-based ring-core 4 for the toroidal coil 3 can be placed, before the cover ply is joined with the intermediate ply. The first conductor segments 5 and the second conductor segments are contacted with one another by through-contacts extending through the plies of the circuit board, so that the first conductor segments, the second conductor segments and the through-contacts form together the continuous windings of the toroidal coil, which surrounds the tape-based ring-core 4.

For protection against media being measured, the coil arrangement 1 has a plastic, protective layer 8 in the wettable region. Preferably, layer 8 completely covers all surfaces of the coil arrangement 1 in the wettable region.

Figure 3:
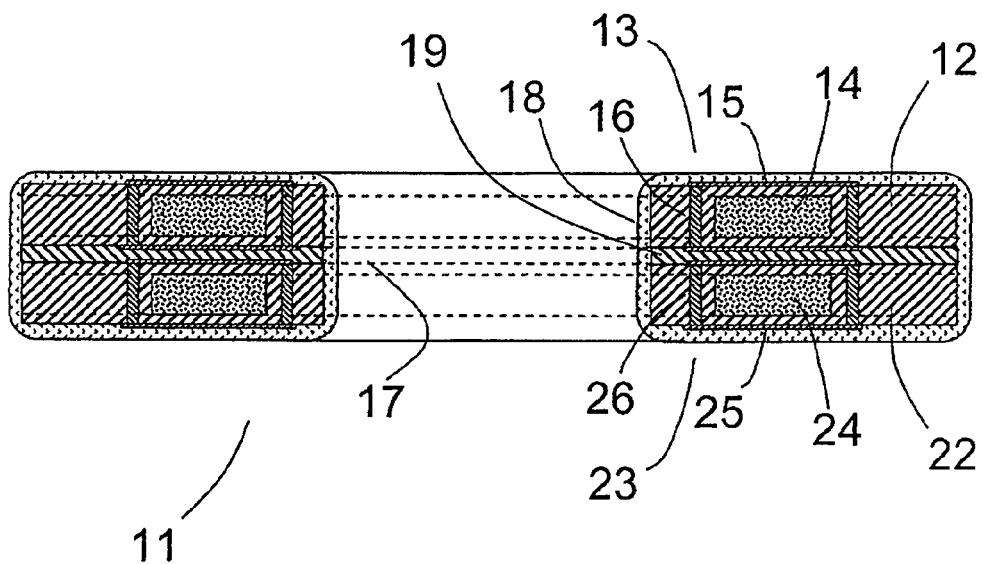
FIG. 3 a longitudinal section through a first example of an embodiment of a sensor head of a conductivity sensor of the invention.

The sensor head 11 of FIG. 3 includes a first toroidal coil 13 and a second toroidal coil 23, both constructed in the manner explained in connection with FIG. 1. The coils 13, 23 are arranged coaxially and axially shifted with respect to one another. Coils 13, 23 each include first and second conductor segments 15, 25, which are contacted together by way of through-contacts 16, 26 through ply portions 12, 22, in order, in each case, to form the continuous windings of the first and second toroidal coils. The two coils are electrically insulated from one another. Extending between the two coils is additionally a separating ply 19, which can comprise one or more ply portions, for example even shielding plies for decoupling the coils. Arranged in cavities in the intermediate plies are, in each case, ring cores 14, 24, surrounded, respectively, by the toroidal coils 13, 23.

The wettable part of the sensor head 11 is, as before, coated with a plastic, protective layer, or coating, 18.

Figure 4:
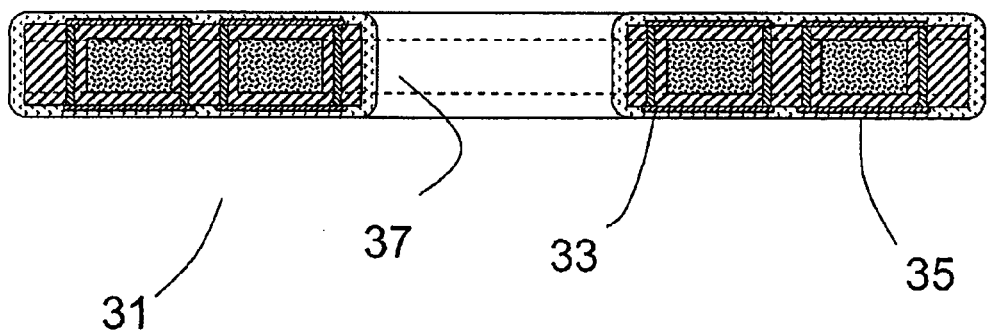
FIG. 4 a longitudinal section through a second example of an embodiment of a sensor head of a conductivity sensor of the invention.

The sensor head 31 in FIG. 4 has two toroidal coils 33, 34 arranged coaxially and coplanarly. Coils 33, 35 bound a passageway 37. Structure of the coils corresponds to the above explanations.

The conductivity sensors of the invention are distinguished by a compact construction and a correspondingly increased sensitivity. Moreover, they can be manufactured with established, automated methods of circuit board production.

What is claimed is:

1. A conductivity sensor for measuring conductivity of a medium surrounding the conductivity sensor, comprising:
   a multi-ply circuit board;
   a first toroidal coil bounding a medium-receiving passageway and serving for inducing an electrical current in the medium; and
   a second toroidal coil also bounding the passageway and serving for registering a magnetic field produced by the electrical current, wherein:
   at least one of the toroidal coils has a plurality of first conductor segments, which extend in a plane of said multi-ply circuit board, a plurality of second conductor segments, which extend in a second plane of said circuit board, and a plurality of through-contacts, which connect said first conductor segments with said second conductor segments;
   said first conductor segments, said second conductor segments and said through-contacts form, together, the windings of a toroidal coil; and
   when said first toroidal coil and said second toroidal coil are surrounded by the medium, said first toroidal coil can be operated as an exciter coil, inducing an electric current in the medium, the current being registered by said second toroidal coil.

2. The conductivity sensor as claimed in claim 1, wherein: said through-contacts extend essentially perpendicularly to the plies of said circuit board.

3. The conductivity sensor as claimed in claim 1, wherein: said first and said second, conductor segments are, in each case, embodied as conductive traces on an outer surface of said circuit board or on an intermediate ply in said circuit board.

4. The conductivity sensor as claimed in claim 1, wherein: at least one of said toroidal coils comprises an air coil.

5. The conductivity sensors claimed in claim 1, wherein: at least one of said toroidal coils comprises a ring-core coil.

6. The conductivity sensor as claimed in claim 5, wherein: said ring-core is arranged in a cavity in said circuit board between the first and second planes.

7. The conductivity sensor as claimed in claim 5, wherein: said ring-core comprises one of: a solid ring-core, a wound-tape ring-core and a plastic ring-core with magnetic particles.

8. The conductivity sensor as claimed in claim 1, wherein: both toroidal coils have a plurality of first conductor segments, which extend in a plane of said multi-ply circuit board, a plurality of second conductor segments, which extend in a second plane of said circuit board, and a plurality of through-contacts, which connect said first conductor segments with said second conductor segments; and
   said first conductor segments, said second conductor segments and said through-contacts together, in each case, form the windings of the respective, two toroidal coils.

9. The conductivity sensor as claimed in claim 1, wherein: said first toroidal coil and said second toroidal coil are arranged coaxially and axially shifted relative to one another.

10. The conductivity sensor as claimed in claim 9, wherein: said first and said second toroidal coil are separated from one another by at least a shielding ply for magnetically and capacitively decoupling the coils.

11. The conductivity sensor as claimed in claim 1, wherein: said first toroidal coil and said second toroidal coil are arranged coaxially and coplanarly.

12. The conductivity sensor as claimed in claim 1, wherein said first toroidal coil and said second toroidal coil annularly bound said medium-receiving passageway, said passageway comprising a bore in the multi-ply circuit board running essentially perpendicularly to said plane and said second plane of said circuit board.

13. A conductivity sensor for measuring conductivity of a medium surrounding the conductivity sensor, comprising:
   a multi-ply circuit board;
   a first toroidal coil bounding a medium-receiving passageway and serving for inducing an electrical current in the medium; and
   a second toroidal coil also bounding the passageway and serving for registering a magnetic field produced by the electrical current, wherein:
   at least one of the toroidal coils has a plurality of first conductor segments, which extend in a plane of said multi-ply circuit board, a plurality of second conductor segments, which extend in a second plane of said circuit board, and a plurality of through contacts, which connect said first conductor segments with said second conductor segments;
   said first conductor segments, said second conductor segments and said through-contacts form, together, the winding of a toroidal coil;
   said first toroidal coil comprises a first ring-core and said second toroidal coil comprises a second ring-core; and
   said first ring-core and said second ring-core are arranged coaxially and axially shifted relative to one another.

14. The conductivity sensor as claimed in claim 13, wherein:
   said first ring-core and said second ring-core are separated from one another by at least one ply of the multi-ply circuit board; and
   a plurality of conductor segments are arranged between said first ring-core and said second ring-core.

15. The conductivity sensor as claimed in claim 13, wherein:
said through-contacts extend essentially perpendicularly to the plies of said circuit board.

16. The conductivity sensor as claimed in claim 13, wherein:
said first and said second, conductor segments are, in each case, embodied as conductive traces on an outer surface of said circuit board or on an intermediate ply in said circuit board.

17. The conductivity sensor as claimed in claim 13, wherein:
said ring-cores are arranged in a cavity in said circuit board between the first and second planes.

18. The conductivity sensor as claimed in claim 13, wherein:
said ring cores comprise one of: a solid ring-core, a wound-tape ring-core and a plastic ring-core with magnetic particles.

19. The conductivity sensor as claimed in claim 13, wherein:
both toroidal coils have a plurality of first conductor segments, which extend in a plane of said multi-ply circuit board, a plurality of second conductor segments, which extend in a second plane of said circuit board, and a plurality of through-contacts, which connect said first conductor segments with said second conductor segments; and
said first conductor segments, said second conductor segments and said through-contacts together, in each case, form the windings of the respective, two toroidal coils.

20. The conductivity sensor as claimed in claim 19, wherein:
said first and said second toroidal coil are separated from one another by at least a shielding ply for magnetically and capacitively decoupling the coils.

21. The conductivity sensor as claimed in claim 19, further comprising:
electronic circuits on said multi-ply circuit board for operation of the sensor.

22. The conductivity sensor as claimed in claim 13, wherein said first toroidal coil and said second toroidal coil annularly bound said medium-receiving passageway, said passageway comprising a bore in the multi-ply circuit board running essentially perpendicularly to said plane and said second plane of said circuit board.

23. A conductivity sensor for measuring conductivity of a medium surrounding the conductivity sensor, comprising:
a multi-ply circuit board;
a first toroidal coil bounding a medium-receiving passageway and serving for inducing an electrical current in the medium; and
a second toroidal coil also bounding the passageway and serving for registering a magnetic field produced by the electrical current, wherein:
at least one of said toroidal coils has a plurality of first conductor segments, which extend in a plane of said multi-ply circuit board, a plurality of second conductor segments, which extend in a second plane of said circuit board, and a plurality of through-contacts, which connect said first conductor segments with said second conductor segments;
said first conductor segments, said second conductor segments and said through-contacts form, together, the windings of a toroidal coil;
said first toroidal coil comprises a first ring-core and said second toroidal coil comprises a second ring-core, said first toroidal coil and said second toroidal coil are arranged coaxially and coplanarly; and
between said first ring-core and said second ring-core said plurality of through-contacts are arranged.

24. The conductivity sensor as claimed in claim 23, wherein:
said through-contacts extend essentially perpendicularly to the plies of said circuit board.

25. The conductivity sensor as claimed in claim 23, wherein:
said first and said second, conductor segments are, in each case, embodied as conductive traces on an outer surface of said circuit board or on an intermediate ply in said circuit board.

26. The conductivity sensor as claimed in claim 23, wherein:
said ring cores are arranged in a cavity in said circuit board between the first and second planes.

27. The conductivity sensor as claimed in claim 23, wherein:
said ring cores comprise one of: a solid ring-core, a wound-tape ring-core and a plastic ring-core with magnetic particles.

28. The conductivity sensor as claimed in claim 23, wherein:
both toroidal coils have a plurality of first conductor segments, which extend in a plane of said multi-ply circuit board, a plurality of second conductor segments, which extend in a second plane of said circuit board, and a plurality of through-contacts, which connect said first conductor segments with said second conductor segments; and
said first conductor segments, said second conductor segments and said through-contacts together, in each case, form the windings of the respective, two toroidal coils.

29. The conductivity sensor as claimed in claim 28, further comprising:
electronic circuits on said multi-ply board for operation of the sensor.

* * * * *